(12) United States Patent
Stauffer (10) Patent No.: US 9,360,659 B2
(45) Date of Patent: Jun. 7, 2016

(54) METHOD FOR PRESENTING AND EVALUATION OF IMAGES OF MICRO-TITER PLATE PROPERTIES

(75) Inventor: Loren Alan Stauffer, Narvon, PA (US)

(73) Assignee: Molecular Devices, LLC, Sunnyvale, CA (US)

( * ) Notice: Subject to any disclaimer, the term of this patent is extended or adjusted under 35 U.S.C. 154(b) by 384 days.

(21) Appl. No.: 14/238,121

(22) PCT Filed: Aug. 9, 2012

(86) PCT No.: PCT/US2012/050067
§ 371 (c)(1),
(2), (4) Date: Feb. 10, 2014

(87) PCT Pub. No.: WO2013/023017
PCT Pub. Date: Feb. 14, 2013

(65) Prior Publication Data
US 2014/0210981 A1    Jul. 31, 2014

Related U.S. Application Data

(60) Provisional application No. 61/522,089, filed on Aug. 10, 2011.

(51) Int. Cl.
| | |
|---|---|
| *G02B 21/00* | (2006.01) |
| *G01B 11/06* | (2006.01) |
| *G01N 21/25* | (2006.01) |
| *G01N 21/13* | (2006.01) |

(52) U.S. Cl.
CPC .............. *G02B 21/002* (2013.01); *G01B 11/06* (2013.01); *G01N 21/253* (2013.01); *G01N 2021/135* (2013.01)

(58) Field of Classification Search
CPC ....................................................... G01B 11/06
USPC ............................................................ 348/79
See application file for complete search history.

(56) References Cited

U.S. PATENT DOCUMENTS

| | | | | |
|---|---|---|---|---|
| 5,757,502 A | * | 5/1998 | Weling | G01B 11/24 356/630 |
| 7,646,482 B2 | * | 1/2010 | Jiang | G01N 21/253 356/326 |
| 2008/0117421 A1 | * | 5/2008 | Yamaguchi | G01J 3/02 356/417 |
| 2009/0086314 A1 | * | 4/2009 | Namba | G01N 21/6458 359/383 |

FOREIGN PATENT DOCUMENTS

GB   2337815 A  * 12/1999  ............. G01B 11/06

OTHER PUBLICATIONS

EP Supplemental Search Report reported May 4, 2015 (searched Apr. 20, 2015) for related European Patent Application No. 12821372.5, and references cited therein.

* cited by examiner

*Primary Examiner* — Jefferey Harold
*Assistant Examiner* — Justin Sanders
(74) *Attorney, Agent, or Firm* — Bella Fishman (57) ABSTRACT

Selected properties of a microplate comprising a plurality of sample wells are obtained by repetitively performing focusing functions to determine sequentially a well surface z-position and then a plate bottom z-position for a corresponding current x-y position based on an intensity indicative of a best focus of the well surface and the plate bottom respectively. The well surface z-position and the plate bottom z-position corresponding to each of the plurality of x-y positions are determined by repeating the steps of positioning the objective lens, performing the focusing function to determine the well surface z-position, and performing the focusing function for the plate bottom z-position. The well surface z-positions and the plate bottom z-positions at the plurality of x-y positions are used to generate data to determine the selected properties of the microplate.

14 Claims, 6 Drawing Sheets

METHOD FOR PRESENTING AND EVALUATION OF IMAGES OF MICRO-TITER PLATE PROPERTIES

RELATED APPLICATION

This application claims priority to provisional application U.S. Ser. No. 61/522,089, filed on Aug. 10, 2011, entitled "METHOD FOR PRESENTING AND EVALUATION OF IMAGES OF MICROTITER PLATE PROPERTIES" in which is incorporated by reference herein.

TECHNICAL FIELD

This invention relates to imaging systems used in examining physical, chemical or biological characteristics of samples in multiple well sample plates, and more particularly to systems and methods for acquiring images for evaluation and presentation of sample plate properties.

BACKGROUND

Materials and objects typically analyzed visually using an imaging system may be analyzed using image acquisition systems capable of handling multiple samples using some level of automation. Such image acquisition systems typically include a light source (such as for example, a white light or a fluorescent light source), a multiple sample plate, and an objective lens optically coupled to an image recording medium (or for example, a camera) to capture an image of the sample that may be substantially magnified. The multiple sample plate may rest or fit onto a sample-positioning mechanism that moves the plate in the optical path of the light source and objective lens. Examples of automated multiple-sample imaging systems include for example, microscopes and analyzers, such as analyzers that may use imaging for analysis of images captured in performing assays. One example of a type of automated imaging system is a high content screening system in which the high-resolution imaging and analysis of samples is automated. The analysis may entail recognizing and segmenting objects, and extracting the features of interest for high content image analysis typically requires the use of high content visualization tools. One particular example of a high content screening system is the Leica HCS A made by Leica Microsystems.

Image acquisition systems may acquire images of samples placed in multiple sample plates implemented as microwell or microplates having a plurality of wells or cavities. It is noted that alternative terms, such as for example, "microwell," "microtiter," and "microplate," are used herein as reference to the plates. The samples are placed in wells arranged in a matrix within the microwell plate.

The Leica HCS A uses a software component called the High Content Screening LAS AF ("Leica Application Suite Advanced Fluorescence") MATRIX M3 automation software. The Leica HCS A system also includes a confocal microscope system. The LAS AF MATRIX M3 automation software includes an autofocus function that permits acquisition of images, which may be used to generate a focus map. A focus map is an automatically generated three-dimensional image showing true sample topology. The focus map is used for Z-positioning of the object of interest during the scan. According to the size and planarity of the samples, the optimal number and positions of the autofocus points is defined.

Another example of an imaging system is the CellReporter™, which is manufactured by Molecular Devices, LLC. The CellReporter™ includes high-quality, quantitative, data image analysis software to image, analyze, and report on individual cells. In capturing images for analysis, the CellReporter™ creates a 3D topological map, or surface map, of the plate-cell attachment surface. Prior to imaging the samples, each plate is scanned while images obtained thereafter are displaying the overall base of the plate. The surface map is used to represent the whole plate contours. In this particular application, the surface map is used to maintain focus across each plate during imaging to eliminate the need to focus at each well before taking an image.

The conventional microplate structure comprises a specimen plate portion with wells or cavities, and a bottom plate portion. The well bottom, or surface at the bottom of each well, is the plate-cell attachment surface of each well. The surface of the microplate opposite the well bottoms is the plate bottom. The distance between plate bottom and the well bottoms defines the thickness of the microplate. The thickness of the microplate may range between about 10 μm and about 1500 μm depending on the manufacturer.

The structure and specification of the microplates play an important role when used in the system to record images with high resolution (X, Y resolution to 100 nm, Z resolution to 300 nm) and high magnification (with 4× magnification and higher). Certain problems in obtaining in-focus images of the wells with samples therein are caused by out-of-focus light measurements. In particular, the problem in obtaining unfocused images in the well with samples is caused by incorrect determination of the focal plane. The incorrect assignment of the focal plane may be caused by variations in the microtiter plates' properties, for example flatness or the thickness of the plate.

The microplates may comprise between 6 and 1536 sample wells or cavities. Such plates are manufactured by a number of companies using a variety of materials. The flatness of the well bottoms and of the plate bottom varies substantially, not only from one manufacturer to another but even from different manufacturing lots. The thickness of the microplate typically varies substantially along the surface of the plate, which may result in incorrect assignment of the focal plane during images.

The importance of the microplate well flatness in obtaining high quality images has been noted by researchers and manufacturers. For example, researchers at GE Healthcare Bio-Sciences Corporation evaluated the 96 and 384-well Marti-Plate™ by performing the same assays on a number of microplates so that the biological evaluations on the different plates under test could be compared. Imaging background measurements were made on all plates by measuring fluorescence intensity background areas of selected images; average background gray levels were measured on a selected number of wells in each plate. Plate flatness data was obtained taking the .xdce file output from each image stack, which contained information on the autofocus position for each image. The information on the autofocus position for each image was used to produce a surface plot for each type of plate. The flatness of the plate well was assessed by taking measurements from several fields of view across three wells in each plate type. For each plate type, positions were abstracted from the .xdce file and plotted as a bar graph. The variation of the autofocus position within a given well reveals its flatness deviation.

This method may be used to label microplates with flatness characteristics, which enables a user to select microplates with desired flatness characteristics. However, a number of manufacturers are not conducting this type of experiment with their microplates, or characterizing their microplates in terms of flatness. Flatness characterization has not been made a part of their process for microplate evaluation, and accordingly, flatness characteristics are not part of the manufacturing specifications of the microplates. Moreover, the different manufacturing processes of the microplates make it difficult or impossible to provide the flatness characteristics for the plate bottom and for the bottom of the wells within the plate.

Therefore, there is a need for automated measurement and visualization of microwell plate information on the flatness of the bottom of the plate and the bottom of the wells for obtaining high quality images in high content screening of samples.

There is also a need for improved and efficient evaluation and presentation of microplate properties, especially with respect to the variation of the thickness along the microplate bottom portion via automated measurements, and to display these properties for acquiring "in focus" microscopy images.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a method is provided for determining selected properties of a microplate comprising a plurality of sample wells. Each sample is open at a top portion of the microplate and includes a well surface receding into the microplate to a well bottom. The well surface is disposed on the top portion opposite a bottom portion of the microplate. An example method includes the step of moving the microplate to position an initial x-y position on the microplate in an optical path generated by a laser. An objective lens is positioned to be substantially centered in the optical path in a z-direction to an initial z-position. A focusing function is performed to determine a well surface z-position for a current x-y position based on an intensity indicative of a best focus of the well surface. The focusing function is performed again to determine a plate bottom z-position for the current x-y position based on an intensity indicative of a best focus of the plate bottom.

The microplate is then repeatedly moved to position a plurality of x-y positions within a selected area of the microplate in the optical path. The selected area encompasses the well bottom of one of the wells on the microplate. At each of the plurality of x-y positions, the well surface z-position and the plate bottom z-position corresponding to each of the plurality of x-y positions are determined by repeating the steps of positioning the objective lens, performing the focusing function to determine the well surface z-position, and performing the focusing function for the plate bottom z-position. The well surface z-positions and the plate bottom z-positions at the plurality of x-y positions are then used to generate data to determine the selected properties of the microplate.

According to another implementation, a system is provided for determining selected properties of a microplate comprising a plurality of sample wells. An example system comprises a focusing laser for generating a focusing light along an optical path. An objective lens is substantially centered at the optical path and mounted on an objective lens support. The objective lens support includes z motor components configured to move the objective lens along a z-axis. An x-y stage supports the microplate and includes x-y motor components configured to move the x-y stage to selected positions on an x-y plane. A light sensor is positioned in the optical path to receive light reflected from the microplate. The light sensor senses an intensity level of the light reflected from the microplate.

The system includes a controller to control the focusing laser, the z motor components, and the x-y motor components. The controller also detects the intensity level measured by the light sensor. The controller comprises a computer-implemented microplate evaluation system, which is configured for:

a. performing a focusing function to determine a well surface z-position for a plurality of x-y positions in a selected area of the microplate encompassing one of the wells based on an intensity indicative of a best focus of the well surface;

b. performing the focusing function to determine a plate bottom z-position for the plurality of x-y positions in the selected area based on an intensity indicative of a best focus of the plate bottom;

c. moving the microplate to position the plurality of x-y positions within the selected area of the microplate in the optical path to perform the focusing functions; and d. using the well surface z-positions and the plate bottom z-positions at the plurality of x-y positions to generate microplate data to determine the selected properties of the microplate.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Disclosed herein are systems, methods, and apparatuses for evaluating and determining properties of microplates. Examples of the systems, methods, and apparatuses may be used in any suitably equipped imaging system such as a high content screening system, or a system that performs assays for diagnostic purposes using imaging to display the results. The description below refers to an imaging system in which advantageous use may be made of the examples described below. It is to be understood that the reference to microplates, imaging systems, or any other example structure is without limitation.

It is noted that the term "microplate" as used below refers to any multiple sample plate having a plurality of wells or cavities. The samples to be analyzed are placed in wells arranged in a matrix within the microplate. It is noted that alternative terms, such as for example, "microwell" or "microtiter" may also be used to refer to a microplate. It is to be understood that the terms "microwell," "microtiter," and "microplate" may be used interchangeably in the description below.

It is to be understood that the term "sample" refers to any material, object or composition that may be placed in a well of a microplate.

Figure 1:
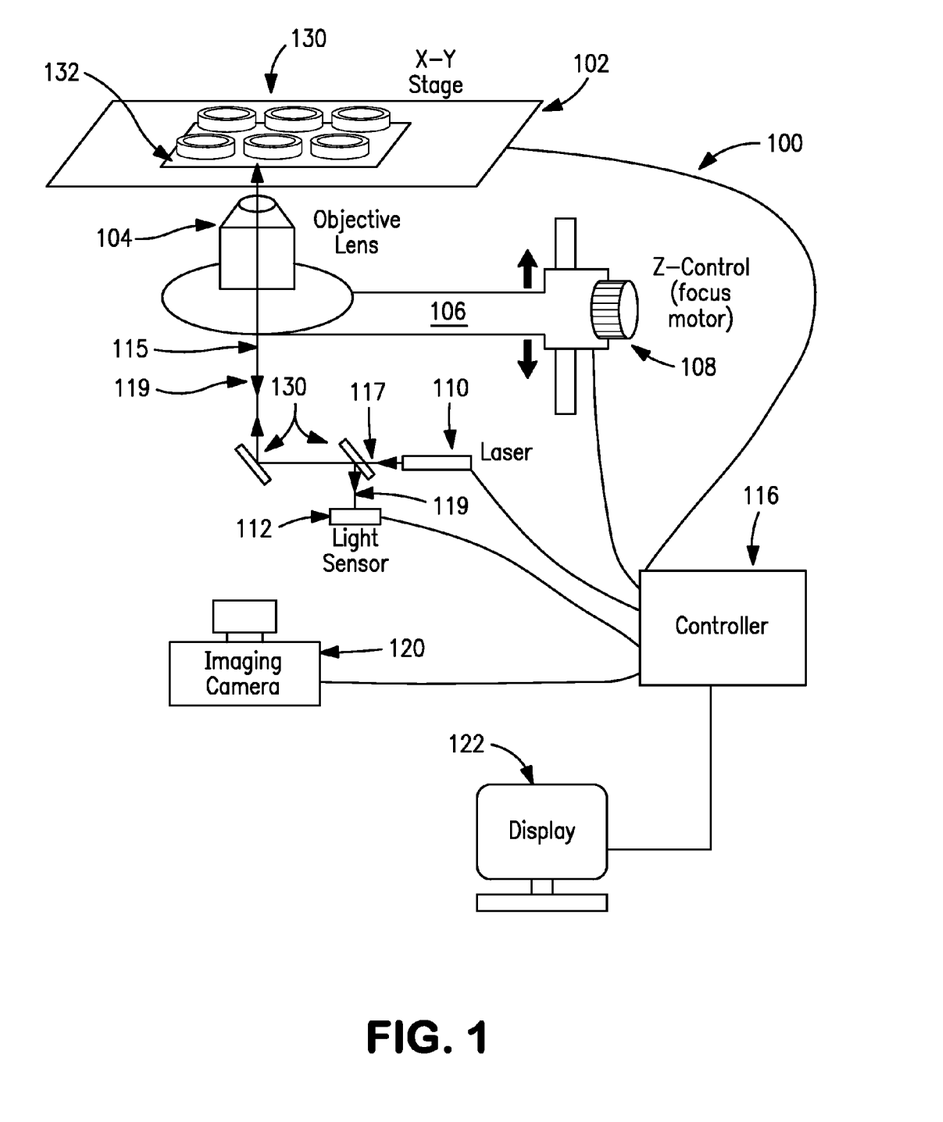
FIG. 1 is a block diagram of an example of a system for determining microplate properties.

FIG. 1 is a block diagram of an example of a system 100 for determining microplate properties. The system 100 includes an x-y stage 102, an objective lens 104, an objective lens support 106, a focusing laser 110, a light sensor (or, laser focus detector) 112, and a controller 116. The system 100 may be implemented in an imaging system that may further include an imaging camera 120 and a display 122. The system 100 may operate as a standalone system for evaluating microplates and storing microplate data corresponding to individual microplates for use in analyzing data collected for samples using the individual microplates. The system 100 may be integrated in an imaging system as components built-in as part of the imaging system. The system 100 may also be implemented as a feature provided in a kit for later integration with the imaging system, such as for example, after manufacture of the imaging system. Such a kit may include a storage medium containing a computer program that implements the functions of the system 100 and components that may not already be part of the imaging system. For example, the focusing laser 110 and the light sensor 112 may be components of such a kit.

The x-y stage 102 may be, or may be similar to, an x-y stage typically implemented on systems used to analyze samples. As shown in FIG. 1, a microplate 130 is mounted on the x-y stage 102 for evaluation of selected properties. The x-y stage 102 includes x-y motor components (not shown in FIG. 1) that moves the x-y stage 102 under control of the controller 116 to selected positions corresponding to points on the microplate 130. The x-y stage 102 moves along a plane corresponding to the substantially planar configuration of the microplate to x-y positions that may be identified using a calibration function. Such calibration functions that associate numerical x positions (along an x-axis of the plane of the motion of the x-y stage 102) and numerical y positions (along the y-axis) to physical points on the microplate are well known to those of ordinary skill in the art, and therefore require no further description.

The objective lens 104 may be any lens suitable for focusing the light from the focusing laser 110 on a point on an object on the x-y stage 102. The objective lens 104 may be positioned so that an optical path 115 created when the focusing laser 110 is emitting light passes substantially at the center of the objective lens 104. In terms of an x-y plane coplanar with the x-y plane defining the space in which the x-y stage 102 moves, the objective lens 104 has a substantially fixed location. The objective lens 104 is configured as shown in FIG. 1 to move in a z-axis direction perpendicular to the x-y plane. The objective lens 104 may be mounted or fixed to the objective lens support 106, which may include z-motion components 108 to move the objective lens 104 in the z-axis direction. The objective lens support 106 and the z-motion components 108 may include a z-reference indicator for homing and calibration of the motion of the objective lens 104 along the z-axis.

The optical path 115 may be directed using optics, such as mirrors, lenses, or splitters. FIG. 1 shows an optical path guide 114 that may be implemented with a mirror and a beam splitter to guide the optical path 115 of a focusing light 117 towards the objective lens 104, and to guide the optical path 115 of a reflected light 119 from the microplate 130 to the light sensor 112. The optical path guide 114 may be implemented using conventional optics components to guide the optical path 115 in conventional ways to ensure the focusing light 117 and the reflected light 119 are properly directed as needed in specific implementations.

The focusing laser 110 may be any laser suitable for generating a light that may be focused in a region near the x-y stage 102. The specific laser used for the focusing laser 110 may depend on the light sensor 112 used. The focusing laser 110 should also have a suitable power rating.

The light sensor 112 may be any suitable photosensitive device having a suitably linear electrical response to light intensity levels. Examples of photosensitive devices that may be used include, without limitation, a phototransistor, a photodiode, a photomultiplier tube, and a photoresistor. In an alternative implementation, the light sensor 112 may be implemented using an imaging device, which may include a camera, or components that capture images using for example a CCD ("charge-coupled device") or a CMOS camera. The light sensor 12 may be implemented in an example implementation using the imaging device used by the imaging system to analyze samples. For example, if the system 100 is implemented to operate using components of an imaging system, of which the system 100 may be an enhancement feature function, the system 100 may use the imaging camera of the imaging system to detect the laser focus.

The example system 100 shown in FIG. 1 depicts an imaging camera 120 that is a component of the imaging system in which the system 100 may be implemented. The imaging camera 120 may be mounted so as to receive the reflected light 119 of the optical path 115 during evaluation of a microplate 130 if the imaging camera 120 is also being used for the functions described herein for the light sensor 112. Alternatively, the imaging camera 120 is used for the primary purpose of the imaging system such as in analyzing samples in the wells of the microplate 130. If the system 100 includes the light sensor 112 for detecting the laser focus during evaluation of the microplate 130, the optical path guide 114 may be switched, or inserted into the optical path 115, to direct the optical path 115 for evaluation functions.

The system 100 in FIG. 1 includes the controller 116, which controls the z-motion components 108, the motion of the x-y stage 102, the focusing laser 110, the light sensor 112, and the imaging camera 120. The controller 116 may control the motion of the x-y stage 102, and the z-motion components 108 by controlling corresponding motors. The controller 116 may control the focusing laser 110 by turning the laser 110 on or off. The controller 116 may communicate with the light sensor 112 to receive intensity levels. The controller 116 may also interface with a display 122 as well as with other user interface devices to allow the operator to view displayed results, and to provide user input.

The controller 116 may be any suitable processing device or system that includes memory and other computing resources. In an example implementation, the controller 116 includes memory or a memory interface to access a computer-implemented microplate evaluation system. The microplate evaluation system may be implemented, for example, as software having functions, such as for example, a function for obtaining microplate data from which selected microplate properties may be determined. In an example implementation, the computer-implemented microplate evaluation system may perform methods such a method for determining microplate properties illustrated by the flowchart in FIG. 3.

The computer-implemented microplate evaluation system analyzes microplates by constructing an image of the microplate 130 from points of best focus along the z-axis at points on an x-y plane that are within a specified area of the microplate 130. The specified area may be defined to include several, or all, of the wells of the microplate as shown at 132. The specified area may also be defined to include a single well as shown at 134 in FIG. 1. The area of interest is mainly the bottom part of the wells on the microplate. The general structure of the microplate 130 may be considered in specifying the area containing the points of primary interest.

Figure 2:
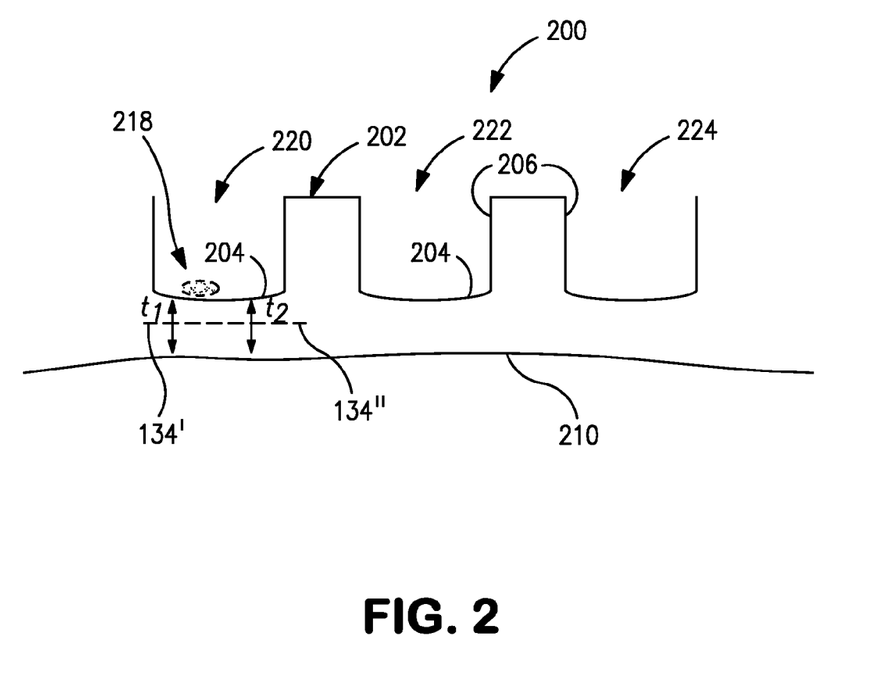
FIG. 2 is a schematic diagram illustrating the structure of a conventional microplate.

FIG. 2 is a cross-sectional view of a portion of a microplate illustrating the structure of a conventional microplate 200. In general, the microplate 200 includes a top surface 202 and a bottom surface 210. The top surface 202 (indicated as being the "top" surface for convenience) provides openings to a first well 220, a second well 222, and a third well 224. Each well 220, 222, 224 includes a well bottom 204 and well sides 206. When the microplate 200 is in use, a sample 218 may be placed in the first well 220, for example. The sample 218 sits on the well bottom 204.

As noted above, the variations in the flatness of the well bottoms 204 may affect the focus during imaging of the sample 218 for analysis of the sample 218. In an example method for determining microplate properties, the image constructed of the microplate structure provides data that may be used to analyze the flatness of the well bottoms 204 and other physical properties of the microplate 200. The properties of the microplate 200 may be determined by evaluating the changes in thickness of the area formed by the well bottoms 204 between the surface of the well bottoms 204 and the bottom surface 210 of the microplate 200. For example, FIG. 2 shows a first thickness, $t_1$, at one point of the surface of the well bottom 204 of the first well 220, and a second thickness, $t_2$, at another point of the same well 220. To determine the selected microplate properties at the first well 220, best focus points for the surface of the well bottom 204 and the bottom surface 210 may be identified at x-y points within an area identified by a line indicating a cross-section 134'-134" encompassing the surface of the well bottom 204 of the first well 220 in FIG. 2. Similar areas may be specified to encompass the wells 222, 224.

Figure 3:
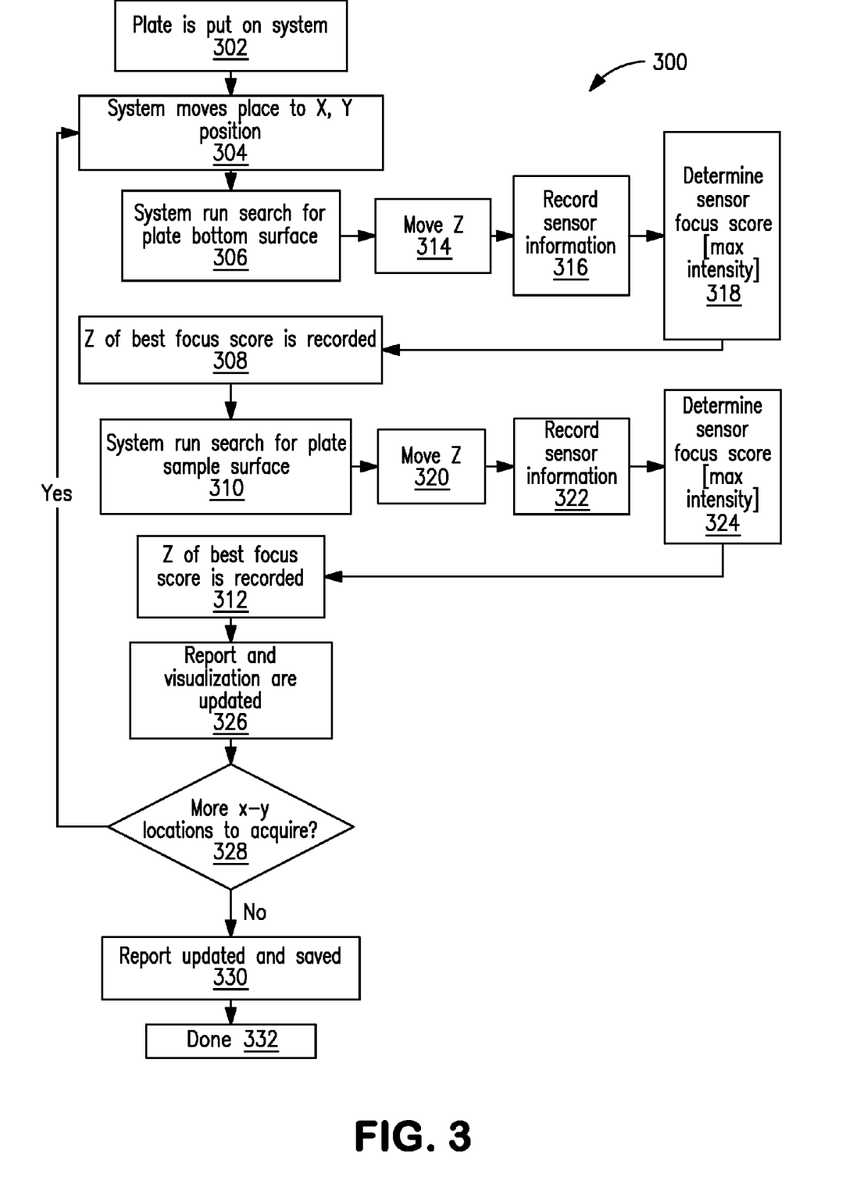
FIG. 3 is a flowchart illustrating operation of an example method for determining microplate properties.

FIG. 3 is a flowchart illustrating operation of an example method 300 for determining microplate properties. The method 300 illustrated in FIG. 3 may be used to evaluate a single well, or to obtain data that may be processed to identify the placements of multiple wells based on the geometry of the microplate 200 as shown in FIG. 2. Once the method 300 is performed for an area that encompasses more than one well, the data may be analyzed to determine where each well is located in terms of the x-y plane of the microplate 200. The wells may be identified by determining where the thicknesses (such as $t_1$ and $t_2$) change dramatically and identifying the locations of dramatic changes as being the side walls 206 of the wells (see FIG. 2).

The method 300 illustrated by the flowchart of FIG. 3 is described as follows in the context of the system 100 shown in FIG. 1. Component actors in the steps of the method 300 refer to the components in FIG. 1 unless stated otherwise. With the focusing laser 110 in the 'on' state, the method 300 in FIG. 3 is started by placing the microplate 130 on the x-y stage 102 as indicated at step 302. At step 304, the x-y stage 130 is then moved so that a selected point on the microplate 130 identified by an x, y position is in the optical path 115. With the x-y stage 102 at the selected x,y position, a search is performed along the z-axis to identify the z-position of the plate bottom surface 210 as shown at step 306. The search is performed by first moving the objective lens 106 along the z-axis at step 314. At each z-position, an intensity level is retrieved from the light sensor 112 at step 316. As intensity levels are collected, a focus score is determined to identify the z-position that provides the best focus of the plate bottom 210 at step 318. The z-position of best focus of the plate bottom 210 is identified as the plate bottom z-position at step 308 for the current x,y position.

At step 310, a search is started to determine the z-position of the surface of the well bottom 204 (in FIG. 2). The search is performed by first moving the objective lens 106 along the z-axis at step 320. At each z-position, an intensity level is retrieved from the light sensor 112 at step 322. As intensity levels are collected, a focus score is determined to identify the z-position that provides the best focus of the surface of the well bottom at step 324. The z-position of best focus of the surface of the well bottom 204 is identified as the well bottom z-position at step 312.

At step 326, the data for any reports or for images of the well that is being collected is updated to indicate the z-position of the plate bottom and the z-position of the well bottom surface for the microplate at the given x,y position. At step 328, a check is made to determine if there are any other x,y positions in the specified area that require determination of the z-positions of the plate bottom and the well bottom. If there are, the next x,y position is determined and the x-y stage 102 is moved to the next x,y position at step 304. If the specified area has been covered, the report for the specified area is updated and stored at step 330. Step 330 may involve creating a database record of z-positions at the x-y positions in the specified area for an identified well. Depending on the area (encompassing a single well, or multiple wells), the database record may contain data for multiple wells. The method may be complete at step 332 for a single well, then repeated for a next well in the microplate. Or, the data may be processed to identify individual wells based on the general geometry of the microplate.

It is noted that in some imaging systems, such as, for example, confocal imaging systems, autofocusing functions may be integrated into the operation of the imaging system. The autofocusing functions, or components of the autofocusing functions, may be used to perform, for example, one or more of steps 306, 314, 316, 318, 308, 310, 320, 322, 324, and 312 in FIG. 3.

The method 300 illustrated by the flowchart in FIG. 3 performs steps of recording sensor information (steps 316 and 322, for example), and the steps are described as determining an intensity level. In the examples described herein, the intensity level indicates the amount of light reflected from the surface of the plate at either the well bottom surface or the plate bottom when the objective lens is at the appropriate distance from the plate. The best focus position is also deemed to be the point at which the intensity level measured is at a maximum out of a group of measurements. It is to be understood by those of ordinary skill in the art that the term 'intensity level' in the context of the steps performed in the method 300 illustrated in FIG. 3 may be a value read off the sensor, or a value that has been processed to either transform the measured value to an actual intensity value, or to scale or normalize the value to simplify the processing. The term 'intensity level' may refer, for purposes of this description, to any parameter indicative of the amount of light reflected from the plate.

The microplate data recorded using the method 300 in FIG. 3 is used to automatically measure and display microwell plate properties. The microplate data may be presented and displayed in a 3D format. The 3-D representation of the microplate data may be especially useful in evaluating the variation of the thickness of the wells and the plate bottom. The 3-D representation may provide a visual display of the contours of the microplate as a whole in addition to the contours of the individual well bottoms.

The microplate properties may be automatically measured and displayed for multiple locations within individual wells. The measured information may provide the user with feedback on the currently imaged microplate during data acquisition in a real-time format. For example, the imaging system may be performing an analysis of samples. The system for determining microplate properties may be used in real-time to retrieve microplate data, and provide the user with information on the microplate properties in real-time during imaging data acquisition. Alternatively, the microplate data for the microplate being used in imaging data acquisition may be retrieved from memory that stores microplate data for previously screened microplates. The system may include user interface tools and functions that permit manipulation of the displayed plate bottom and well bottom images. For example, such manipulation may allow the user to rotate, or zoom-in and zoom-out or to perform other operations. The images displaying the data for the plate bottom and well bottom may be presented as 3-D or 2-D color-coded diagram.

The microplate data that characterizes the plate bottom and well bottom may be collected and stored to conduct automated analysis and to produce reports requested by users. The reports may be used, for example, in a certification system when the manufacturer of an acquisition device certifies that microplate models are compatible with the device, or when certification is required to validate acquisition device accuracy when using a known microplate. Multiple microplates of the same model from the same manufacturer may be analyzed to determine the extent of the variation of the properties of microplates within a manufacturing lot or between different manufacturing lots. The measured data from a plurality of microplates may also be used to automatically adjust acquisition settings during analysis of samples.

The results obtained from comparing the properties of multiple microplates may provide information relating to whether particular microplates "failed" or "passed" some desired certification standard. The results may also provide information regarding the overall quality of the microplates. The microplate properties for multiple microplates may also provide a historical record that may be used to adjust acquisition settings for performing imaging of samples. The historical record may be stored as images acquired from various microplates. The analysis of the numerical data may include for example, selecting minimum, maximum and average thickness of each well. The information relating to the numerical values obtained by analysis of the numerical data of the microplate properties may be used to set positions and ranges to optimize the focus speed for the acquisition imaging systems used for analyzing samples.

The information relating to the optimization of the acquisition settings may include, for example, indications that the setting ranges are too narrow, which may further indicate that the optimization of the acquisition settings is not allowing the next attempt to obtain focus. In addition, the information may indicate if the setting ranges are too broad, which may extend the time to obtain each focus. The provided information may also indicate whether or not the plate is damaged or, for some other reason does not match the required criteria. The 3-D visual display of the properties, and more particularly, the thickness of the plate bottom and well bottom, allows for inspection and comparison of the results of such inspection with requested microplate's property.

After the acquisition settings are optimized, a procedure may be used to obtain feedback on setting quality during analysis of a sample. Feedback procedures may be invoked and the data may be analyzed using the user interface.

The microplate properties data may be stored for multiple microplates to monitor quality and equipment compatibility control. For example, when the thickness property of the microplate is accurately defined and displayed, the process of selecting the microplates for testing on the instrumentation becomes more transparent and efficient for user.

Figure 4:
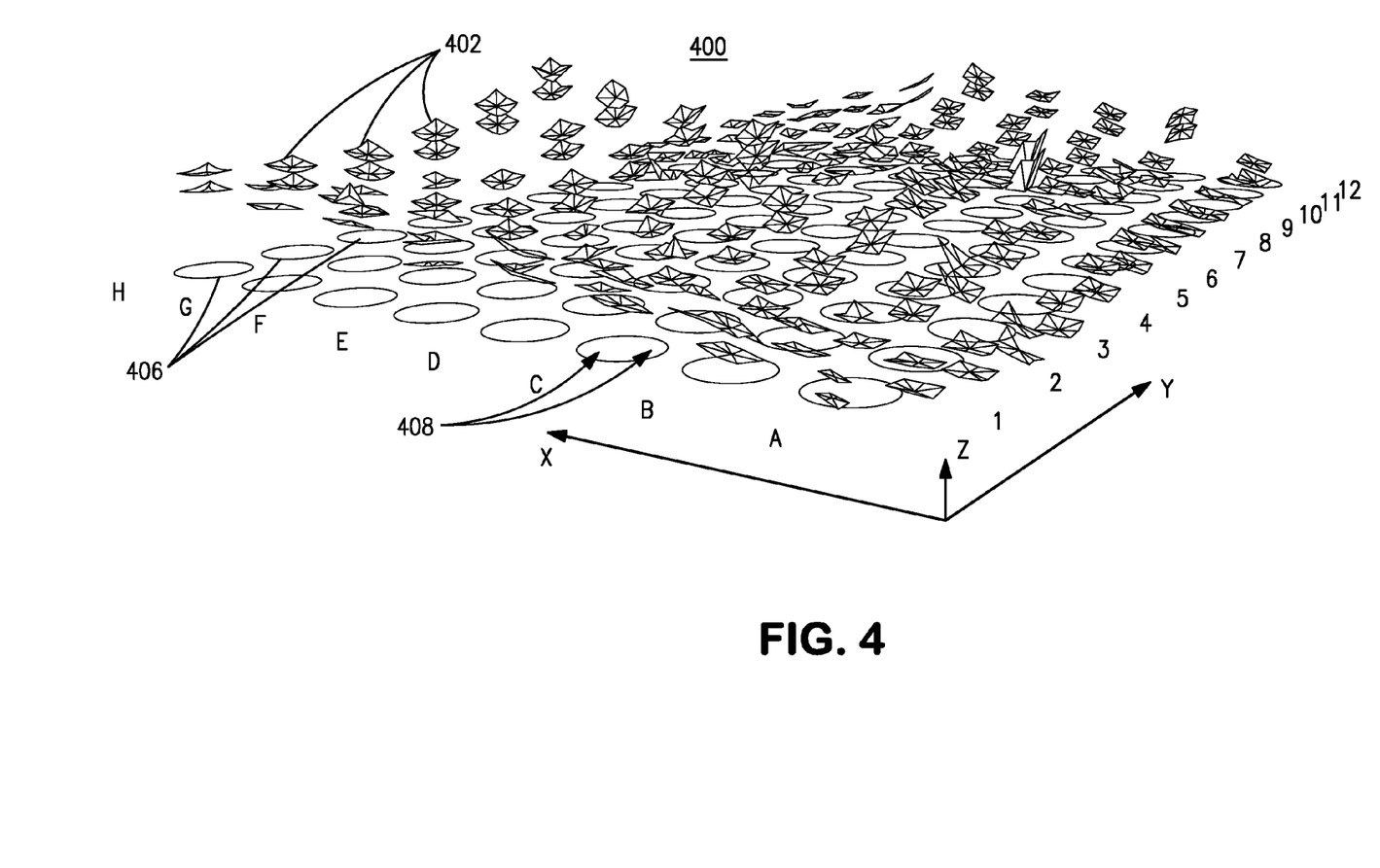
FIG. 4 is a diagram illustrating an example of a 3-D visualization of multiple points within a well in a microplate.

FIG. 4 is a diagram illustrating an example of a 3-D visualization 400 a section of a microplate. The 3-D visualization 400 in FIG. 4 depicts multiple top regions 402 indicating a plate top surface and corresponding bottom regions 404 indicating a plate bottom surface. It is noted that the 3-D visualization 400 is displayed with the z-axis to a different scale than the x and y axes in order to better visualize the well and plate contours. The top and bottom regions 402 and 404 are shown positioned over corresponding specified areas of measurement 406. The specified areas of measurement 406 contain dots 408 indicating x-y positions for which a plate bottom z-position and a well surface z-position have been determined. Rulers for x and y axis positions may be displayed to provide the user with indication of location on the plate. The data for the 3-D visualization 400 in FIG. 4 may be collected in real-time as the 3-D visualization 400 is displayed. When generated in real-time, the 3-D visualization 400 may indicate the progress of the imaging by depicting the filling of the specified areas 406 with dots 408. The 3-D visualization 400 may be displayed as data is collected during a screening of the microplate performed to evaluate the microplate. The 3-D visualization 400 may also be displayed during image acquisition for analyzing samples.

Figure 5:
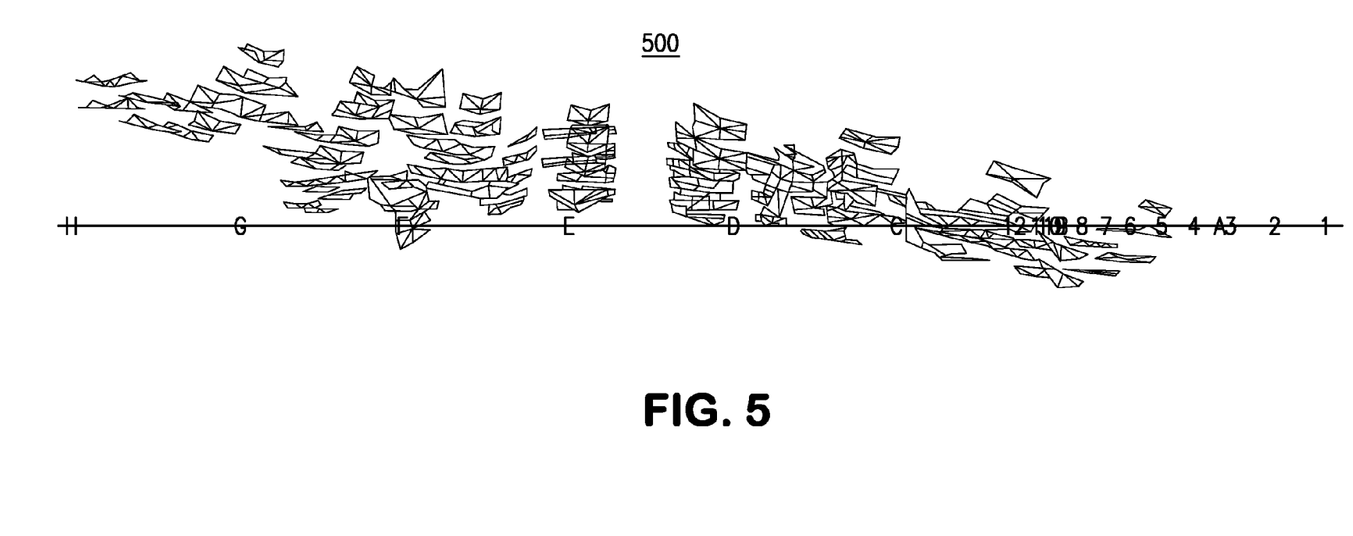
FIG. 5 is a diagram illustrating the 3-D visualization of FIG. 4 after it has been rotated to show a side view of the well.

FIG. 5 is a diagram illustrating the 3-D visualization of FIG. 4 after it has been rotated to show a side view 500 of the microplate.

A 3-D visualization such as the 3-D visualization 400 in FIG. 4 and the side view 500 in FIG. 5 may include status information indicating the status of each focus attempt used to create the 3-D visualization. The status information may be conveyed using combinations of colors, shapes or other unique visual characteristics that may be configured to indicate the success or failure of each focus attempt, as well as of the type of focus performed.

The microplate data may be used to generate visualization of the data in other forms. For example, the microplate data may be used to plot a heat map to display microplate-based image analysis data that may be used to display:

1. Z-axis variation within a well,
2. the moving from site-to-site,
3. the variation among adjacent wells moving from well-to-well, or
4. the variations in bottom thickness.

Figure 6:
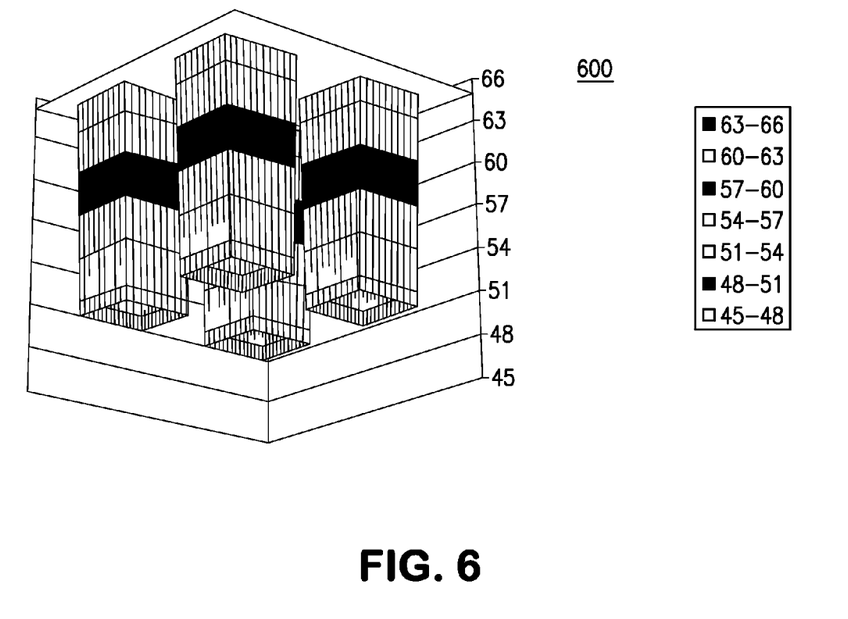
FIG. 6 is a diagram illustrating an example of a surface map generated using model data for representing the well bottom positions in a 3-D image.

FIG. 6 is a diagram illustrating an example of a surface map 600 generated using model data for representing the well bottom positions in a 3-D image. The model data represents hypothetical values for well bottom surface positions and plate bottom positions for a model microplate. The surface map 600 in FIG. 6 shows the well bottom positions across the microplate, which illustrates the thickness variation along the bottom of the microplate. The surface map 600 in FIG. 6 was created using the Microsoft Excel™ application, however, any suitable spreadsheet or imaging application that constructs images from data representing positions on a surface may also be used.

It will be understood that various aspects or details of the invention may be changed without departing from the scope of the invention. Furthermore, the foregoing description is for the purpose of illustration only, and not for the purpose of limitation—the invention being defined by the claims.

What is claimed:

1. A method for determining selected properties of a microplate comprising a plurality of sample wells, each sample well being open at a top portion of the microplate and including a well surface, the well surface being disposed on the top portion opposite a plate bottom of the microplate, the method comprising:
   moving the microplate to position an initial x-y position on the microplate in an optical path generated by a laser;
   positioning an objective lens substantially centered in the optical path in a z-direction to an initial z-position;
   performing a focusing function to determine a well surface z-position for a current x-y position based on an intensity indicative of a best focus of the well surface;
   performing the focusing function to determine a plate bottom z-position for the current x-y position based on an intensity indicative of a best focus of the plate bottom;
   moving the microplate to position a plurality of x-y positions within a selected area of the microplate in the optical path where the selected area encompasses the well bottom of one of the wells on the microplate;
   at each of the plurality of x-y positions, determining the well surface z-position and the plate bottom z-position corresponding to each of the plurality of x-y positions by repeating the steps of positioning the objective lens, performing the focusing function to determine the well surface z-position, and performing the focusing function for the plate bottom z-position; and
   using the well surface z-positions and the plate bottom z-positions at the plurality of x-y positions to generate an image in a 3-D format to depict the well bottom and plate bottom; and
   to display the image on a display to illustrate a flatness of the well bottom, the flatness of the well bottom being one of the selected properties of the microplate.

2. The method of claim 1, further comprising:
   moving the microplate to position an initial x-y position in a next area encompassing another well on the microplate in the optical path;
   determining the well surface z-position and the plate bottom z-position for each x-y position in the next area; and
   repeating the steps of moving the microplate to an area encompassing another well and of determining the well surface z-position and the plate bottom z-position for each x-y position in the area until data for determining the selected properties of the microplate has been generated for a selected plurality of wells on the microplate.

3. The method of claim 1, where the step of using the well surface z-positions and the plate bottom z-positions at the plurality of x-y positions includes determining a plate thickness between the well bottom and the plate bottom in the area encompassing a selected well, the plate thickness being one of the selected properties of the microplate.

4. The method of claim 2, where the step of using the well surface z-positions and the plate bottom z-positions at the plurality of x-y positions includes generating a surface or a heat map by:
   generating a surface map comprising well images representing well bottom positions for the wells within the specific areas for which well surface and plate bottom focusing was performed; and
   displaying the surface map on a display to display well bottom positions on the surface map.

5. The method of claim 2, where the step of using the well surface z-positions and the plate bottom z-positions at the plurality of x-y positions to generate the heat map includes:
   generating well images representing well bottom positions for the wells within the specific areas for which well surface and plate bottom focusing was performed; and
   displaying the heat map on a display to display z-axis variation within wells, variation among adjacent wells, or variations in bottom thickness.

6. The method of claim 2, where the step of using the well surface z-positions and the plate bottom z-positions at the plurality of x-y positions to generate the 3-D image includes:
   generating well images representing well bottom positions for the wells within the specific areas for which well surface and plate bottom focusing was performed;
   displaying the 3-D image on a display; and
   receiving user interface commands to either zoom in, zoom out, or rotate the 3-D image about an axis.

7. The method of claim 1, further comprising indicating a success or failure of the steps of performing the focus functions.

8. The method of claim 1, where the step of performing the focus function to determine the well surface z-position for a current x-y position includes:
   measuring an intensity of light reflected from the microplate at a sensor in the optical path as the objective lens is moved to a plurality of z-positions; and
   determining a best focus z-position corresponding to the intensity indicative of a best focus of the well surface.

9. The method of claim 1, where the step of performing the focus function to determine the plate bottom z-position for a current x-y position includes:
   measuring an intensity of light reflected from the microplate at a sensor in the optical path as the objective lens is moved to a plurality of z-positions; and
   determining a best focus z-position corresponding to the intensity indicating a best focus of the plate bottom.

10. A system for determining selected properties of a microplate comprising a plurality of sample wells, each sample well being open at a top portion of the microplate and including a well surface, the well surface being disposed on the top portion opposite a plate bottom of the microplate, the system comprising:
    a focusing laser for generating a focusing light along an optical path;
    an objective lens substantially centered at the optical path and mounted on an objective lens support that includes z motor components configured to move the objective lens along a z-axis;
    an x-y stage configured to support the microplate, the x-y stage comprising x-y motor components configured to move the x-y stage to selected positions on an x-y plane;
    a light sensor positioned in the optical path to receive light reflected from the microplate and to sense an intensity level of the light reflected from the microplate; and
    a controller being implemented in a personal computer configured to control the focusing laser, the z motor components, and the x-y motor components, and to detect the intensity level measured by the light sensor, further comprising a computer-implemented microplate evaluation system configured for:

performing a focusing function to determine a well surface z-position for a plurality of x-y positions in a selected area of the microplate encompassing one of the wells based on an intensity indicative of a best focus of the well surface;

performing the focusing function to determine a plate bottom z-position for the plurality of x-y positions in the selected area based on an intensity indicative of a best focus of the plate bottom;

moving the microplate to position the plurality of x-y positions within the selected area of the microplate in the optical path to perform the focusing functions; and using the well surface z-positions and the plate bottom z-positions at the plurality of x-y positions to generate an image in a 3-D format to depict the well bottom and plate bottom; and to display the image on a display to illustrate a flatness of the well bottom, the flatness of the well bottom being one of the selected properties of the microplate;

the controller, the laser, the light sensor, x-y stage and objective lens being integrated into an imaging system, wherein the computer-implemented microplate evaluation system is configured to be added after manufacture of the imaging system.

11. The system of claim 10, where the light sensor is a photosensitive device that generates an electrical signal having a parameter that changes in response to the intensity of the light received by the photosensitive device.

12. The system of claim 10, where the personal computer with the controller implemented therein communicating with the focusing laser, the z motor components, the x-y motor components, and the light sensor via a communication interface.

13. The system of claim 12, where the personal computer comprises:
 a display; and
 a database configured to store microplate profiles each comprising microplate data corresponding to a specific microplate.

14. The system of claim 10, further comprising a display-to-display images generated using the microplate data, where the images are formatted to depict selected properties of the microplate.

* * * * *